United States Patent [19]

Schmidt

[11] 4,262,668

[45] Apr. 21, 1981

[54] FIXED VOLUME INFUSION DEVICE

[75] Inventor: Bradley J. Schmidt, East Dundee, Ill.

[73] Assignee: Baxter Travenol Laboratories, Inc., Deerfield, Del.

[21] Appl. No.: 27,910

[22] Filed: Apr. 6, 1979

[51] Int. Cl.³ .............................................. A61M 5/00
[52] U.S. Cl. ............................... 128/214 R; 222/450; 137/179
[58] Field of Search ............ 128/214 R, 214 C, 214 G, 128/214 Z; 222/189, 445, 450–452; 137/173, 177, 179; 251/331

[56] References Cited

U.S. PATENT DOCUMENTS

| 4,030,495 | 6/1977 | Virag | 128/214 F |
|---|---|---|---|
| 4,072,292 | 2/1978 | Banon | 251/331 |
| 4,121,584 | 10/1978 | Turner | 128/214 E |
| 4,136,693 | 1/1979 | Dyke | 128/214 C |
| 4,142,523 | 3/1979 | Stegeman | 128/214 R |
| 4,142,524 | 3/1979 | Jassawalla et al. | 128/214 F |
| 4,185,759 | 1/1980 | Zissimopoulos | 222/450 |

Primary Examiner—Dalton L. Truluck
Attorney, Agent, or Firm—Paul C. Flattery; John A. Caruso; Gary W. McFarron

[57] ABSTRACT

A flow regulator is disclosed for controlling the intravenous infusion of parenteral solution or the like to a patient. The solution flows through passageways in a housing, including a fixed volume portion. Fluid control means upstream and downstream of the fixed volume portion alternately open and close inlet and outlet passageways to periodically fill and empty the fixed volume portion, which is vented to allow displacement air to enter or exit. Hydrophobic filter means are provided in the vent path to permit venting but to prevent the escape of liquid. Hydrophilic filter means are provided downstream of the fixed volume portion to prevent gas or air from passing to the patient. The alternate opening and closing of the fluid control means in the inlet and outlet passageways permits a maximum fixed volume of liquid to be dispensed to the patient.

9 Claims, 3 Drawing Figures

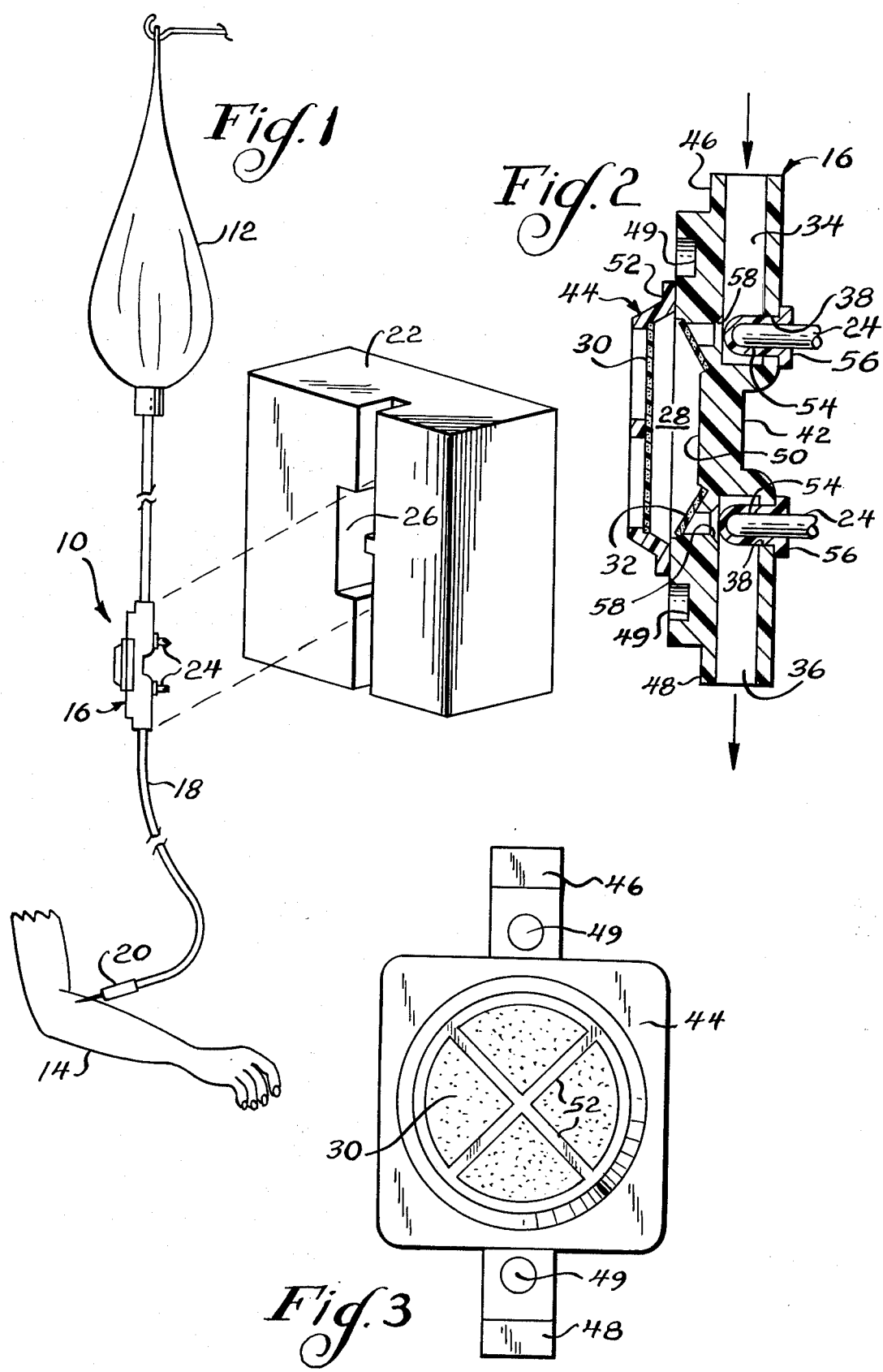

FIXED VOLUME INFUSION DEVICE

The present invention relates generally to intravenous fluid infusion controllers and, more particularly, to controllers which provide incremental fixed volume dispensing of fluid to the patient.

A variety of flow control techniques are used for administering intravenous fluids to a patient, ranging from the simple roller clamp, such as is shown in U.S. Pat. No. 3,099,429, to precise fluid metering pumps, as illustrated in U.S. Patent Application Ser. No. 759,178, filed Jan. 13, 1977. Between these two extremes, there is a need for a relatively low cost but accurate metering device for intravenous fluids. Recently, a flow control device has been provided which precisely controls the gravitational discharge of intravenous fluid into the patient. As shown in U.S. Pat. No. 4,121,584, a flow controller is provided which has a chamber defined, in part, by a flexible diaphragm. Valves upstream and downstream of the diaphragm alternately open the chamber to the influx of fluid and release the fixed volume of fluid for infusion into the patient. This device is particularly advantageous in preventing too much fluid from being infused into the patient.

The flow control device described above uses a chamber defined between a portion of the housing and a diaphragm that flexes between a position adjacent the housing and a position spaced from the housing to define the closed interior chamber. Although the flexible diaphragm is very successful, it does require fairly precise assembly techniques and, in some cases, reinforcement to prevent damage by the valving action, which uses a pinching force against the diaphragm to open and close the flow passageways to the fixed volume chamber.

Accordingly, it is a general object of the present invention, to provide a fixed volume infusion control device that does not suffer the deficiencies described above.

It is a more specific object of the present invention to provide a fixed volume infusion control device which does not employ a flexible diaphragm to define a fixed volume chamber.

It is a further object of the present invention to provide an incremental flow control device which does not require reinforcing or the like to prevent puncture or damage of the components of the control device.

It is yet another object of the present invention to provide a fixed volume control device which filters the infusing liquid as it passes to the patient.

These and other objects of the present invention are set forth in the following detailed description of the attached drawings, of which:

FIG. 1 is an elevational view of a flow control device embodying the present invention employed in a gravitational flow intravenous fluid administration set.

FIG. 2 is a vertical sectional view of the flow control device of FIG. 1 embodying the present invention.

FIG. 3 is a front view of the flow control device illustrated in FIGS. 1 and 2.

The present invention is generally embodied in a gravitational intravenous fluid flow system 10 for administering intravenous fluids, e.g., saline solution, from an elevated fluid reservoir 12 to the patient 14. An incremental fluid control device 16 is mounted in-line with the plastic tubing 18 which extends from the reservoir to a needle hub or luer connector 20, which may be attached to a needle or catheter placed in the patient's vascular system. The fluid control device 16 is adapted for placement into a controller, schematically illustrated at 22. The controller has a pair of oscillating control arms, shown broken away at 24, which alternatingly open and close the fluid passageways into the control device 16. For ease in use, the control device 16 is designed for insertion into a frontal slot 26 in the controller, much like a tape cassette. Accordingly, the control device 16 will be referred to hereinafter as a fluid control cassette. Details of such a construction for the controller is shown in more detail in the aforementioned U.S. Pat. No. 4,121,584.

In accordance with the present invention, the unique fluid control cassette 16 does not employ a flexible diaphragm for defining a fixed volume chamber but, rather, includes a fixed volume portion 28 defined, at least in part, by hydrophobic filter means 30 and hydrophilic filter means 32 which, respectively, permit air to vent from the chamber to the atmosphere as it is filled with liquid but prevent air or gas from passing to the patient. Intravenous fluid flows to and from the fixed volume chamber 28 via fluid passageway in the cassette, which includes an inlet portion 34 and outlet portion 36, respectively upstream and downstream of the fixed volume portion 28. Apertures or ports 38 are provided in the housing in each passageway portion. Fluid control means in the form of movable plugs 40 are carried within the apertures and are movable to open and close the fixed volume portion or chamber 28, to alternately allow filling and emptying of said portion with a specifically defined quantity of liquid.

Turning now to a more detailed description of the preferred embodiment of the present invention, shown in the attached drawings for the purpose of illustration and not limitation, the cassette 16 includes a two-piece plastic housing, with a base portion 42 and a cap 44. The base portion is generally shaped for receipt in the controller 22. As best seen in FIG. 3, the base has a generally square center portion with an inlet arm 46 at the top through which inlet passageway 34 passes, and an outlet arm 48 at the bottom, through which outlet passageway 36 passes. A pair of guide openings or slots 49 may be provided in the housing for assuring alignment with matching devices in the controller.

Referring back to FIG. 2, the inlet passageway 34 is generally L-shaped and communicates with a center circular-dished recessed area 50 in the body portion. The outlet passageway 36 is also L-shaped and similarly communicates with the recessed area 50, but on the opposite side from the inlet passageway.

The cap 44 is sized to cover the recessed area to define the fixed volume or chamber 28 therebetween. The cap has an annular rim 52 which may be sealed, by heat, solvent bonding, adhesive or the like to the body portion. The cap has a large center opening approximately the same diameter as the recess 50, spanned by a reinforcing grid defined by crossing bridge members 52. To cover the opening in the cap and prevent the escape of liquid therethrough, hydrophobic filter means 30 in the form of a filter membrane, which is substantially impervious to liquid but pervious to gas or air, spans the opening on the inside of the cap. The filter is sealed around its peripheral edge to the cap so that liquid cannot escape from the housing. The hydrophobic membrane is preferably made of polytetrafluoroethylene, commonly known as Teflon plastic, which is naturally liquid repellent. The filter is positioned on the inside of the cap so that as fluid flows into the chamber 28, the grid formed by bridging members 52 reinforce the hydrophobic membrane and prevent outward flexure which may result in membrane damage.

In general, the intravenous fluid flows through the inlet passageway 34, the chamber 28 and the outlet passageway 36. To prevent air from passing to the patient from the chamber 28, a hydrophilic filter means in the form of a membrane is mounted over the L-shaped outlet passageway. When wetted, this material permits liquid to pass but is impervious to gas or air. At the same time, the filter, which is microporous and has a pore size of preferably less than 0.5 microns, effectively filters particulate and even bacteria from the fluid stream as it is administered to the patient. Although not required, it may also be desirable to have a similar hydrophilic membrane spanning the inlet passageway to the chamber 28, thereby providing dual filtration as well as a dual barrier to the passage of gas from upstream of the cassette.

The cassette 16 precisely limits the amount of fluid infused into the patient by alternately opening and closing the fixed volume chamber 28 to the influx of liquid. This is accomplished by fluid control means upstream and downstream of the chamber. In the illustrated embodiment, apertures 38 are provided in the base portion 42, communicating with the L-shaped passageways upstream and downstream of the chamber 28. The apertures are generally co-axial with one of the legs of the respective L-shaped passageways, which leads to the chamber.

Positioned within each aperture 38 is a hollow elastomeric plug 54, made of rubber, silicone or similar medically approved material. The plug is closed at the end positioned within the L-shaped passageway, and has an annular rim 56 overlapping the outside edge of the aperture 38. These plugs are adapted to receive the control arms, shown in part at 24, of the controller 22. The plugs are normally in an open position, and oscillating movement of the control arms alternately move the closed end of the plug against an annular seat or surface 58 which surrounds the co-axial branch of the particular L-shaped passageway.

During operation, the control arms 24 cooperate so that the lower control arm closes the outlet passageway 36 while the upper control arm is released to allow fluid flow into the chamber 28. Fluid flows through the inlet passageway 34, and if provided, through the uppermost hydrophilic membrane adjacent the inlet passageway. Air within the chamber is displaced by the liquid and vents through the hydrophobic filter membrane 30 which covers the inside of the open cap 44. The controller is timed so that the inlet is open a sufficient length of time to permit the chamber 28 to be filled. Because the hydrophobic membrane is about the same size as the chamber, the chamber is able to fill completely without any substantial residue of unvented air remaining. The controller then simultaneously stretches the inlet control plug 54 to a closed position, tightly against the east 58 to block further inlet flow, and the outlet control is released to an open position to permit the liquid accumulated in the chamber to empty to the patient. The liquid passes out of the chamber through the hydrophilic filter membrane 32 and through the L-shaped outlet passageway 36. Fluid flowing out of the chamber 28 is displaced by air passing into the chamber through the hydrophobic membrane 30. This air, however, is not permitted to pass through the patient because the hydrophilic membrane, once wetted is impervious to the passage of air or gas, provided that air or gas does not exceed the "bubble point" of the hydrophilic membrane. Since the air displacing the liquid will be at atmospheric pressure, it will not exceed the bubble point of the hydrophilic material and will not pass through the outlet to the patient.

Thus, it may be seen that with the present invention an incremental fluid control cassette is provided which has minimum moving parts, does not require a flexible diaphragm to alternately define and close a fixed volume chamber, but rather uses the natural displacement of air and liquid to permit the device to function, yet without any danger of air being passed to the patient. At the same time, the fluid is simultaneously filtered of particulate matter, even bacteria, thereby avoiding the need for further down-line filtration. Although the present invention has been described in terms of the illustrated embodiment, it is intended that this invention, as defined in the following claims, cover those equivalent structures, some of which may be apparent upon reading this description and others which may be arrived at only after some study.

What is claimed is:

1. An incremental fixed volume fluid control cassette for use with a flow controller having a pair of movable control arms for controlling flow through said cassette, said cassette comprising:
   a housing;
   a flow passageway through said housing including a fixed volume portion with an inlet and an outlet;
   a pair of spaced apertures in said housing communicating with said flow passageway upstream and downstream of said fixed volume portion;
   fluid control means carried by said housing in each of said apertures, said control means being adapted to engage said control arms for movement alternately into and out of said flow passageway to block or open said flow passageway;
   vent opening in said housing in communication with said fixed volume portion;
   hydrophobic filter means carried by said housing in the path of air venting through said vent opening to prevent the escape of liquid therethrough;
   hydrophilic filter means carried in said flow passageway downstream of said fixed volume portion to prevent the passage of air to the patient.

2. A fluid control cassette in accordance with claim 1 wherein fluid control means comprises an elastomeric plug within each aperture movable between an open position where flow through said flow passageway is permitted and a closed position where flow through said flow passageway is blocked.

3. A fluid control cassette in accordance with claim 2 wherein each of said plugs is hollow to receive a control arm from a controller for movement between open and closed positions.

4. A fluid control cassette in accordance with claim 1 further comprising a second hydrophilic filter carried in said flow passageway adjacent said inlet of said fixed volume portion.

5. An incremental fixed volume fluid control cassette for use with a flow controller, said cassette comprising:
   a two-part housing comprising a body portion and a cap portion, said body portion comprising an inlet flow passageway, an outlet flow passageway and a recess in the surface of said body portion between and communicating in series with said inlet and outlet flow passageways, each of said inlet and outlet passageways being L-shaped with one leg of said passageway communicating with said recess;

a cap carried on said body and covering said recess to define a chamber therebetween, said cap having vent opening means;

hydrophobic filter membrane spanning said vent opening means to permit air to vent from said chamber while preventing liquid from escaping;

hydrophilic filter membrane spanning said outlet flow passageway to filter fluid and prevent the passage of air to the patient;

a pair of spaced apertures in said body portion and communicating with said inlet and outlet passageways on either side of said recess, each of said ports being substantially co-axial with one of the legs of one of said L-shaped passageways;

an elastomeric seal carried in each of said apertures and being movable to engage a peripheral edge portion of said one leg of said L-shaped passageway to block the flow of liquid therethrough.

6. An incremental fixed volume fluid control cassette for use with a flow controller, said cassette comprising:

a housing;

a flow passageway through said housing including a fixed volume portion with an inlet and an outlet;

a pair of spaced apertures in said housing communicating with said flow passageway upstream and downstream of said fixed volume portion;

fluid control means carried by said housing and associated with each of said apertures to block or open said flow passageway;

vent opening in said housing in communication with said fixed volume portion;

hydrophobic filter means carried by said housing in the path of air venting through said vent opening to prevent the escape of liquid therethrough; and hydrophilic filter means carried in said flow passageway downstream of said fixed volume portion to prevent the passage of air to the patient;

said housing being of two-piece construction including a body portion defining said flow passageway upstream and downstream of said fixed volume portion, and a cap carried by said base and defining said fixed volume portion therebetween, said cap including said vent opening and said hydrophobic filter means being a hydrophobic membrane carried by said cap and spanning said vent opening.

7. A fluid control cassette in accordance with claim 6 wherein said fixed volume portion comprises a recess in said body portion, said cap covering and sealing said recess.

8. A fluid control cassette in accordance with claim 4 wherein said cap comprises an annular rim and a supporting grid spanning said rim, said hydrophobic filter carried on the inside surface of said cap and having an edge portion sealed around said annular rim, said grid supporting said filter against outwad flexure.

9. An incremental fixed volume fluid control cassette for use with a flow controller, said cassette comprising:

a housing;

a flow passageway through said housing including a fixed volume portion with an inlet and an outlet;

a pair of spaced apertures in said housing communicating with said flow passageway upstream and downstream of said fixed volume portion;

fluid control means carried by said housing and associated with each of said apertures to block or open said flow passageway;

vent opening in said housing in communication with said fixed volume portion;

hydrophobic filter means carried by said housing in the path of air venting through said vent opening to prevent the escape of liquid therethrough; and hydrophilic filter means carried in said flow passageway downstream of said fixed volume portion to prevent the passage of air to the patient;

said fluid control means comprising a hollow elastomeric plug within each aperture, each of said plugs having an annular rim at one end engaging the edge of said aperture and a closed, rounded interior end portion disposed within said flow passageway, said passageway including an annular seat facing said closed end portion, whereby a control arm from said controller is movable within said plug to stretch said plug until said closed end engages said seat to block flow.

* * * * *